United States Patent [19]

Ascione et al.

[11] Patent Number: 5,607,664
[45] Date of Patent: Mar. 4, 1997

[54] PHOTOPROTECTIVE/COSMETIC COMPOSITIONS COMPRISING UV-A AND/OR UV-B SUNSCREENS AND POLYMERS COMPATIBLE THEREWITH

[75] Inventors: Jean-Marc Ascione, Paris; Delphine Allard, Colombes; Isabelle Hansenne, Paris, all of France

[73] Assignee: L'Oreal, Paris, France

[21] Appl. No.: 463,221

[22] Filed: Jun. 5, 1995

[30] Foreign Application Priority Data

Jun. 3, 1994 [FR] France .................... 94 06836

[51] Int. Cl.$^6$ ................ A61K 7/42; A61K 7/40; A61K 31/74
[52] U.S. Cl. .............. 424/59; 424/60; 424/78.08; 424/401; 514/844
[58] Field of Search .............. 424/59, 60, 401, 424/78.08; 514/844, 938

[56] References Cited

U.S. PATENT DOCUMENTS 5,302,376  4/1994  Forestier et al. ............ 424/59

FOREIGN PATENT DOCUMENTS 0427411  5/1991  European Pat. Off. .
2398496  2/1979  France .

OTHER PUBLICATIONS

Shaath, N., "Encyclopedia of UV Absorbers for Sunscreen Products", Cosmetic & Toiletries, vol. 102 Mar. 1987 pp. 21–36.

Roelandts, R. et al. "A Survey of Ultraviolet Absorbers in Commercially Available Sun Products", International Journal of Dermatology, May 1983, vol. 22, pp. 247–255.

Primary Examiner—Shelley A. Dodson
Attorney, Agent, or Firm—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise (i) a photoprotecting effective amount of at least one organic or inorganic UV screen, or mixture thereof, and (ii) at least one polymer compatible therewith, said at least one polymer comprising recurring structural units of the following formula (I) and recurring structural units of the following formulae (II) and/or (III):

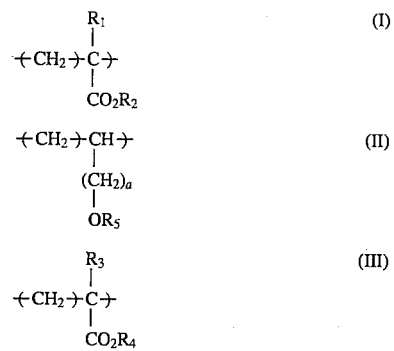

in a cosmetically acceptable vehicle, diluent or carrier therefor which comprises a continuous aqueous phase.

24 Claims, No Drawings

PHOTOPROTECTIVE/COSMETIC COMPOSITIONS COMPRISING UV-A AND/OR UV-B SUNSCREENS AND POLYMERS COMPATIBLE THEREWITH

CROSS-REFERENCE TO COMPANION APPLICATIONS

Copending applications [Attorney Docket No. 016800-029], Ser. No. 08/463,505 [Attorney Docket No. 016800-030], Ser. No. 08/463,503 U.S. Pat. No. 5,489,431 [Attorney Docket No. 016800-031], Ser. No. 08/463,762 [Attorney Docket No. 016800-032], Ser. No. 08/463,304 [Attorney Docket No. 016800-033], Ser. No. 08/463,508 [Attorney Docket No. 016800-034], Ser. No. 08/461,015 [Attorney Docket No. 016800-035], Ser. No. 08/463,507 [Attorney Docket No. 016800-036], Ser. No. 08/464,940 each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions imparting enhanced photoprotection, comprising, in a cosmetically acceptable vehicle, carrier or diluent which comprises a continuous aqueous phase, particularly an oil-in-water emulsion, immixture of (i) at least one conventional photoprotective agent that is a UV screen (whether of UV-A and/or UV-B), including one or more organic sunscreen compounds (UV absorbers) and/or one or more inorganic (nano)pigments based on metal oxides, preferably based on titanium dioxide, that function by physically blocking UV irradiation (UV reflectors and/or UV diffusers), and (ii) at least one judiciously selected particular polymer compatible therewith.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

The inorganic pigments and nanopigments, collectively (nano)pigments, based on metal oxides, especially based on titanium dioxide, are known active materials for solar protection (by "nanopigments" are intended particulates of pigments, the average size of the primary particles of which generally not exceeding 100 nm, and which preferably ranges from 5 nm to 100 nm, even more preferably from 10 nm to 50 nm.)

It too is known that these inorganic materials, whether or not in combination with conventional organic screening compounds absorbing UV-A and/or UV-B irradiation, impart to the sunscreen compositions comprised thereof a certain relatively limited inherent or additional photoprotective characteristic, by physically blocking the UV rays (reflection and/or diffusion).

To improve the essentially cosmetic properties of the sunscreen/cosmetic compositions, and notably of those described above, it is now usual to formulate therein so-called emulsifying polymers, among which the crosslinked copolymers of the acrylic acid/$C_{10}$–$C_{30}$ alkyl acrylate type, such as those marketed under the trademarks "PEMULEN TR-1" and "CARBOPOL 1342" by Goodrich, are representative.

Nonetheless, one of the disadvantages presented by most of the sunscreen/cosmetic compositions which contain such polymers, whether they are based on organic sunscreen compounds or on (nano)pigments, or mixtures thereof, is that their sun protection factors on skin, especially very sensitive skins and/or those continually exposed to the sun, remain insufficient.

Thus, need continues to exist in this art to improve further the photoprotective properties of the known sunscreen compositions, while naturally preserving their good cosmetic properties.

SUMMARY OF THE INVENTION

It has now unexpectedly and surprisingly been determined that formulating certain judiciously selected particular polymers into otherwise conventional sunscreen compositions enhances the photoprotective factors thereof, while maintaining good cosmetic properties, in comparison with the sunscreen compositions known to this art containing emulsifying polymers (at an equal concentration of sunscreen compound(s) and/or of (nano)pigments, in a vehicle of identical kind).

Briefly, the present invention features novel photoprotective/cosmetic compositions comprising, in a cosmetically acceptable vehicle, diluent or carrier which comprises a continuous aqueous phase, immixture of (i) at least one photoprotective agent that is a UV screen (UV-A and/or UV-B) and (ii) at least one polymer selected from among those which comprise recurring structural units of the following formula (I) and recurring structural units of the following formulae (II) and/or (III):

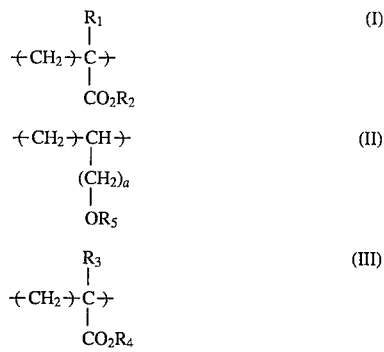

in which g is an integer equal to 0 or 1, $R_1$, $R_2$, $R_3$ and $R_4$, which may be identical or different, are each a hydrogen atom or a $C_1$-$C_4$ alkyl radical, $R_5$ is a $CH_3CO$—radical or a radical $R_6$—$(OC_2H_5)_b$—, wherein $R_6$ is a $C_2$-$C_{20}$ alkyl radical, and b is an integer ranging from 1 to 20, inclusive, with the proviso that, when the polymer is devoid of recurring structural units of formula (II), the radicals $R_2$ and $R_4$ cannot simultaneously be hydrogen atoms.

Consistent herewith, by "photoprotective agent" that is a screen for UV irradiation is intended any compound or mixture of compounds, whether organic and/or inorganic and whether via the mechanisms of absorption and/or reflection and/or diffusion of UV-A and/or UV-B radiation, that prevents or at least limits such radiation from contacting the surface (e.g., human skin and/or hair) to which this/these compound(s) has/have been applied. Thus, this invention comprehends both UV-absorbing photoprotective organic sunscreen compounds and UV-diffusing and/or UV-reflecting inorganic (nano)pigments, as well as mixtures thereof.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

DETAILED DESCRIPTION OF BEST MODE AND PREFERRED EMBODIMENTS OF THE INVENTION

More particularly according to the present invention, the constituent polymers are traditionally prepared via polymerization of the monomer or monomers providing the recurring structural unit(s) desired in the final polymer. Thus, the (co)monomers employed for the synthesis of the polymers of the invention are selected from among the (alkyl)acrylic acids, alkyl acrylates, vinyl alkanoates and allyl or vinyl ethers or esters. As indicated above, the polymers according to the present invention can be either (i) copolymers (copolymerization of two different monomers) simultaneously comprising recurring structural units of formula (I) and recurring structural units of formula (II), or, alternatively, copolymers simultaneously comprising recurring structural units of formula (I) and recurring structural units of formula (III), or (ii) terpolymers (copolymerization of three different monomers) simultaneously comprising recurring structural units of formula (I), recurring structural units of formula (II) and recurring structural units of formula (III).

When the polymer comprises one or more recurring structural units including a carboxyl function, this/these structural unit(s) may be converted, if necessary, into a partially or completely neutralized form, especially by reacting same with alkaline agents and/or by adjusting the pH of the compositions.

In a preferred embodiment of the present invention, the polymers employed are partially or totally crosslinked polymers.

In another preferred embodiment of this invention, from among the polymers described above, the preferred polymers are those which impart a viscosity of at least 5 poises to an aqueous medium into which they are introduced, when used at concentrations ranging from 0.2% to 2% by weight.

Especially preferred polymers according to the present invention include:

(a) crosslinked terpolymers: methacrylic acid/ethyl acrylate/steareth-10 allyl ether (such polymers are marketed, in particular, under the trademark "SALCARE SC 90" by Allied Colloids, and are presented in the form of an aqueous emulsion containing approximately 30% AS);

(b) crosslinked copolymers: acrylic acid/vinyl acetate (such polymers are marketed, in particular, under the trademark "RHEOLATE 5000" by Rhéox);

(c) crosslinked copolymers: acrylic acid/ethyl acrylate (such polymers are marketed, in particular, under the trademark "ACRYSOL 33" by Rohm and Haas, and are presented in the form of an aqueous dispersion containing approximately 30% AS).

The polymers according to the invention are advantageously present in the final sunscreen/cosmetic compositions at a concentration (expressed as active substance AS) ranging from 0.05% to 15% by weight, and preferably from 0.1% to 4% by weight, relative to the total weight of the composition.

As indicated above, the polymers according to the invention may be combined either with one or more UV-absorbing organic sunscreen compounds, or with one or more inorganic (nano)pigments, or, alternatively, with mixtures of these screening agents (screening system).

The metal oxides constituting the pigments or nanopigments suitable for formulation into the sunscreen/cosmetic compositions according to the present invention comprise those which are per se known for their photoprotective activity. Thus, they are advantageously selected from among titanium, zinc, iron, zirconium and cerium oxides, or mixtures thereof.

Preferably, nanopigments of metal oxides are employed.

Such nanopigments of metal oxides, whether coated or uncoated, are materials known to this art and described, in particular in EP-A-0,518,773, hereby expressly incorporated by reference. Additional and commercially available nanopigments not described therein, but which are also suitable according to this invention include the products marketed under the trademarks UVT M 160, UVT M 212 and UVT M 262 by Kemira, and MT 100 SA and MT 100 SAS by Tayca.

As indicated above, the average primary particle size of the nanopigments present in the compositions of the invention generally ranges from 5 nm to 100 nm, preferably from 10 to 50 nm.

In a preferred embodiment of the invention, inorganic nanopigments are employed that are based on titanium dioxide. This titanium dioxide may be in a crystallized state of rutile and/or anatase type, and/or in an amorphous or substantially amorphous form. As indicated above, this pigment either may or may not then be coated, but it is preferable to use coated pigments, for example coated with alumina and/or aluminum stearate.

The nanopigments are typically present in the compositions according to the invention at a concentration ranging from 0.1% to 30% by weight, and preferably from 1% to 20% by weight, relative to the total weight of the compositions.

Similarly, the sunscreen compositions of the invention can, in addition, contain one or more conventional hydrophilic or lipophilic organic sunscreen agents (absorbing agents) which are active in the UV-A and/or UV-B region. Exemplary of such additional sunscreens are 2-phenylbenzimidazole-5-sulfonic acid and salts thereof, cinnamic derivatives such as, for example, 2-ethylhexyl p-methoxycinnamate, salicylic derivatives such as, for example, 2-ethylhexyl salicylate and homomenthyl salicylate, camphor derivatives such as, for example, 3-(4-methylbenzylidene)camphor or (1,4-divinylbenzene)camphorsulfinic acid, triazine derivatives such as 2,4,6-tris[p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, $\beta$, $\beta$-diphenylacrylate derivatives such as 2-ethylhexyl $\alpha$-cyano-$\beta$, $\beta$-diphenylacrylate, p-aminobenzoic acid derivatives such as, for example, octyl and para-dimethylaminobenzoate, menthyl anthranilate and the sunscreen polymers and sunscreen silicones described in WO-93/04,665. Other examples of organic sunscreen agents are described in EP-A-0,487,404.

These organic sunscreen agents are advantageously present in the sunscreen/cosmetic compositions according to the present invention at a concentration ranging from 0.1% to 30% by weight, and preferably from 0.5% to 25% by weight, relative to the total weight of the final composition.

Preferably, the overall content of the screening agents (organic sunscreen compound(s)+ (nano)pigment(s)) does not exceed 40% of the total weight of the final sunscreen/cosmetic composition.

In another preferred embodiment of the present invention, the cosmetically acceptable vehicle diluent or carrier in which the screening agents and the polymer or polymers are contained is an oil-in-water type emulsion. However, any other vehicle in which the continuous phase would actually be an aqueous phase (as in the event of a simple aqueous gel, for example) is also within the scope of this invention.

The compositions according to the invention may also contain agents for the artificial tanning and/or browning of the skin (self-tanning agents) such as, for example, dihydroxyacetone (DHA).

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, $\alpha$-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in the form of oil-in-water emulsions.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-$\alpha$-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water type.

The subject compositions may, in particular, be in the form of a cream, a milk, a gel, an ointment or a cream gel, and may optionally be packaged as an aerosol and may be provided in the form of a foam, a mousse or a spray.

When the subject composition is an oil-in-water emulsion, the aqueous phase of this emulsion may comprise a nonionic vesicle dispersion prepared according to known processes (Bangham, Standish and Watkins, *J. Mol. Biol.*, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products (for the skin, eyelashes, eyebrows, etc.).

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLES

A variety of photoprotective/sunscreen formulations were prepared, in the form of an oil-in-water type emulsion and containing the following (the amounts are expressed as % by weight relative to the total weight of the composition):

| | |
|---|---|
| (a) Nanopigments of $TiO_2$ ("MT 100 T" marketed by Tayca) (average size of the primary particles: 15 nm) | 0 or 5% |
| (b) 2-Ethylhexyl p-methoxycinnamate ("PARSOL MCX" marketed by Givaudan) (organic UV screening agent) | 0 or 5% |
| (c) Polymer (according to and not according to the invention) | x % AS |
| (d) Mixture of glyceryl monostearate and polyethylene glycol stearate containing 100 moles of EO ("ARLACEL 165" marketed by ICI) | 20% |
| (e) Stearic acid | 4% |
| (f) Stearyl alcohol | 1% |
| (g) Petroleum jelly Codex | 3% |
| (h) Liquid petrolatum Codex | 13% |
| (i) Polydimethylsiloxane ("SILBIONE OIL 70 047V 300" marketed by Rhône-Poulenc) | 1% |
| (j) Triethanolamine     qs | pH 6–7 |
| (k) Glycerol | 5% |
| (l) Preservatives | qs |
| (m) Water     qs | 100% |

The polymers examined were the following:
(i) SALCARE SC 90 (crosslinked terpolymer: methacrylic acid/ethyl acrylate/steareth-10 allyl ether, according to the invention), (ii) RHEOLATE 5000 (acrylic acid/vinyl acetate copolymer, according to the invention), (iii) by way of comparison, PEMULEN TR-1 marketed by Goodrich (crosslinked copolymer: acrylic acid/ $C_{10}$–$C_{30}$ alkyl acrylate, not according to the invention), already formulated into certain sunscreen compositions of the prior art.

Each of these emulsions was produced by dissolving the photoprotective/sunscreen agent in the fatty phase, then adding the emulsifiers to this fatty phase, heated to about 80° C, and, lastly, adding, with rapid stirring, the aqueous phase previously heated to this same temperature.

For each of the formulations thus prepared, the sun protection factor (SPF) which was associated therewith was then determined. It was determined using the in vitro technique described by B.L. Diffey et al, in *J. Soc. Cosmet. Chem.*, 40, 127-133 (1989); this technique entailed determining the monochromatic protection factors every 5 nm over a wavelength range of from 290 to 400 nm, and in calculating the sun protection factor from these factors according to a given mathematical equation.

The chemical compositions of the formulations and the results obtained, in terms of a mean protection factor, are reported in the Table below:

TABLE

| | FORMULATIONS | | | | | |
| --- | --- | --- | --- | --- | --- | --- |
| | 1 | 2 | 3 | 4 | 5 | 6 |
| Nanopigments (%) | 5 | 0 | 5 | 0 | 5 | 0 |
| Sunscreen Agent (%) | 0 | 5 | 0 | 5 | 0 | 5 |
| SALCARE SC90 (% AS) | 1.5 | 1.5 | 0 | 0 | 0 | 0 |
| RHEOLATE 5000 (% AS) | 0 | 0 | 0.5 | 0.5 | 0 | 0 |
| PEMULEN TR-1 (% AS) | 0 | 0 | 0 | 0 | 1 | 1 |
| Mean SPF | 8.5 | 8.2 | 6.1 | 9.3 | 2.8 | 6.8 |
| (standard deviation) | (1.4) | (0.6) | (0) | (0.4) | (0.3) | (0.6) |
| | Invention | | | | Comparative | |

These results clearly demonstrate the better photoprotective properties of the compositions according to the invention, both in the presence of organic photoprotective/sunscreen agents and in the presence of nanopigments.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising (i) a photoprotecting effective amount of at least one organic or inorganic UV screen, or mixture thereof, and (ii) at least one polymer compatible therewith, said at least one polymer comprising recurring structural units of the following formula (I) and recurring structural units of the following formulae (II) and/or (III):

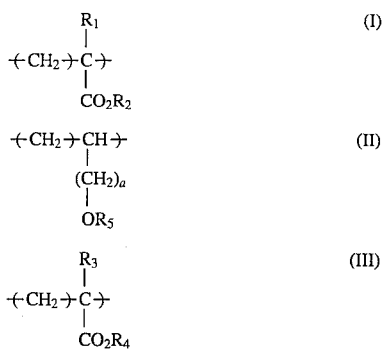

in which a is an integer equal to 0 or 1, $R_1$, $R_2$, $R_3$ and $R_4$, which may be identical or different, are each hydrogen atoms or a $C_1$–$C_4$ alkyl radical, $R_5$ is a $CH_3CO$— radical or a radical $R_6$—$(OC_2H_5)_b$—, wherein $R_6$ is a $C_2$–$C_{20}$ alkyl radical, and b is an integer ranging from 1 to 20, inclusive, with the proviso that, when the polymer is devoid of recurring structural units of formula (II), the radicals $R_2$ and $R_4$ cannot simultaneously be hydrogen atoms, in a cosmetically acceptable vehicle, diluent or carrier therefor which comprises a continuous aqueous phase.

2. The sunscreen/cosmetic composition as defined by claim 1, comprising from 0.05% to 15% by weight of said at least one polymer (ii).

3. The sunscreen/cosmetic composition as defined by claim 2, comprising from 0.1% to 4% by weight of said at least one polymer (ii).

4. The sunscreen/cosmetic composition as defined by claim 1, comprising (i) a photoprotecting effective amount of at least one UV absorbing organic sunscreen and/or at least one inorganic (nano)pigment.

5. The sunscreen/cosmetic composition as defined by claim 4, comprising at least one inorganic (nano)pigment based on the oxides of titanium, zinc, iron, zirconium or cerium, or mixtures thereof.

6. The sunscreen/cosmetic composition as defined by claim 5, comprising at least one inorganic nanopigment.

7. The sunscreen/cosmetic composition as defined by claim 6, said at least one inorganic nanopigment comprising titanium dioxide.

8. The sunscreen/cosmetic composition as defined by claim 7, comprising rutile, anatase or amorphous titanium dioxide.

9. The sunscreen/cosmetic composition as defined by claim 4, comprising from 0.1% to 30% by weight of at least one inorganic (nano)pigment.

10. The sunscreen/cosmetic composition as defined by claim 9, comprising from 1% to 20% by weight of said at least one (nano)pigment.

11. The sunscreen/cosmetic composition as defined by claim 4, comprising from 0.1% to 30% by weight of at least one UV absorbing organic sunscreen.

12. The sunscreen/cosmetic composition as defined by claim 1, said at least one polymer (ii) comprising a crosslinked terpolymer of methacrylic acid/ethyl acrylate/steareth-10 allyl ether, a crosslinked copolymer of acrylic acid/vinyl acetate, or a crosslinked copolymer of acrylic acid/ethyl acrylate.

13. The sunscreen/cosmetic composition as defined by claim 1, comprising an oil-in-water emulsion.

14. The sunscreen/cosmetic composition as defined by claim 4, comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

15. The sunscreen/cosmetic composition as defined by claim 1, further comprising at least one active agent for the artificial tanning and/or browning of human skin.

16. The sunscreen/cosmetic composition as defined by claim 1, further comprising at least one cosmetically acceptable adjuvant or additive.

17. The sunscreen/cosmetic composition as defined by claim 16, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

18. The sunscreen/cosmetic composition as defined by claim 1, comprising a cream, milk, gel, cream gel, ointment, foam, mousse or spray.

19. The sunscreen/cosmetic composition as defined by claim 1, comprising a makeup.

20. A method for protecting human skin and/or hair against the deleterious effects of ultraviolet irradiation, comprising topically applying thereto an effective amount of the sunscreen/cosmetic composition as defined by claim 1.

21. A method for protecting human skin and/or hair against the deleterious effects of solar radiation, comprising topically applying thereto an effective amount of the sunscreen/cosmetic composition as defined by claim 1.

22. The sunscreen/cosmetic composition of claim 1, wherein the polymer is one which imparts a viscosity of at least 5 poises to an aqueous medium when introduced at a concentration ranging from about 0.2% to 2% by weight.

23. The sunscreen/cosmetic composition of claim 1, wherein if the polymer is devoid of recurring structural units of formula (II), then the polymer consists substantially of recurring structural units of formula (I) and recurring structural units of formula (III), wherein in said monomers the radicals $R_2$ and $R_4$ cannot simultaneously be hydrogen atoms.

24. The sunscreen/cosmetic composition of claim 1, wherein if the polymer is devoid of recurring structural units of formula (II), then the polymer consists essentially of recurring structural units of formula (I) and recurring structural units of formula (III), wherein in said monomers the radicals $R_2$ and $R_4$ cannot simultaneously be hydrogen atoms.

* * * * *